United States Patent
Yang et al.

(10) Patent No.: US 11,054,323 B2
(45) Date of Patent: Jul. 6, 2021

(54) QUANTITATIVE IMPACT CONTROL AND MEASUREMENT SYSTEM

(71) Applicant: KOREA INSTITUTE OF SCIENCE AND TECHNOLOGY, Seoul (KR)

(72) Inventors: Sungwook Yang, Seoul (KR); Eui-Sung Yoon, Seoul (KR); Hoon Ryu, Seoul (KR); Hyeonjoo Im, Seoul (KR)

(73) Assignee: Korea Institute of Science and Technology, Seoul (KR)

(*) Notice: Subject to any disclaimer, the term of this patent is extended or adjusted under 35 U.S.C. 154(b) by 375 days.

(21) Appl. No.: 16/199,741

(22) Filed: Nov. 26, 2018

(65) Prior Publication Data
US 2019/0242766 A1  Aug. 8, 2019

(30) Foreign Application Priority Data
Feb. 2, 2018 (KR) .................. 10-2018-0013421

(51) Int. Cl.
*G01L 5/00* (2006.01)
*A61B 5/00* (2006.01)
*A61B 5/103* (2006.01)

(52) U.S. Cl.
CPC .......... *G01L 5/0052* (2013.01); *A61B 5/1036* (2013.01); *A61B 5/4064* (2013.01); *A61B 2503/40* (2013.01); *A61B 2562/0219* (2013.01)

(58) Field of Classification Search
None
See application file for complete search history.

(56) References Cited

U.S. PATENT DOCUMENTS

| 2,755,658 | A | * | 7/1956 | Brown ............... G01P 21/00 73/12.13 |
| 3,759,085 | A | * | 9/1973 | Wilson ............ G01L 5/0052 73/12.09 |
| 5,739,411 | A | * | 4/1998 | Lee ................. G01N 3/48 73/12.09 |
| 6,826,509 | B2 | | 11/2004 | Crisco, III et al. |

(Continued)

FOREIGN PATENT DOCUMENTS

| JP | 3084331 B2 | 9/2000 |
| KR | 10-2005-0104532 A | 11/2005 |

(Continued)

OTHER PUBLICATIONS

Catherine E. Creeley et al., "Multiple Episodes of Mild Traumatic Brain Injury Result in Impaired Cognitive Performance in Mice", Acad Emerg Med, Aug. 2004, pp. 809-819, vol. 11, No. 8.

(Continued)

*Primary Examiner* — Jill E Culler
(74) *Attorney, Agent, or Firm* — Rabin & Berdo P.C.

(57) ABSTRACT

A quantitative impact control and measurement system includes an impactor configured to apply an impact to a target, a control device configured to control movement of the impactor, an acceleration sensor mounted to a base of the impactor, and an impact sensor mounted to a terminal of the impactor. Here, the control device calculates an impact actually applied to the target from signals measured through the acceleration sensor and the impact sensor.

10 Claims, 11 Drawing Sheets

(56) References Cited

U.S. PATENT DOCUMENTS

| | | | | |
|---|---|---|---|---|
| 7,430,892 | B2* | 10/2008 | McNamara | G01N 3/48 |
| | | | | 73/12.13 |
| 9,217,699 | B2* | 12/2015 | Klaas | G01N 3/317 |
| 9,808,193 | B2 | 11/2017 | Tortella et al. | |
| 9,895,099 | B2 | 2/2018 | Rennaker | |
| 2011/0219852 | A1 | 9/2011 | Kasten | |
| 2014/0107523 | A1 | 4/2014 | Petraglia et al. | |
| 2018/0047305 | A1 | 2/2018 | Lee | |

FOREIGN PATENT DOCUMENTS

| | | |
|---|---|---|
| KR | 10-1729905 B1 | 5/2017 |
| KR | 10-2017-0071951 A | 6/2017 |

OTHER PUBLICATIONS

Tsung-Hsun Hsieh et al., "Relationship of mechanical impact magnitude to neurologic dysfunction severity in a rat traumatic brain injury model", PLOS ONE, May 26, 2017, pp. 1-18, vol. 12, No. 5.

* cited by examiner

QUANTITATIVE IMPACT CONTROL AND MEASUREMENT SYSTEM

CROSS-REFERENCE TO RELATED APPLICATION

This application claims priority to Korean Patent Application No. 10-2018-0013421, filed on Feb. 2, 2018, and all the benefits accruing therefrom under 35 U.S.C. § 119, the contents of which in its entirety are herein incorporated by reference.

STATEMENT REGARDING SPONSORED RESEARCH

This study was supported by the brain science source technology development project of the Ministry of Science, ICT and Future Planning (Development of a platform for the implementation of 3D in-vitro neuron/cytoplasmic network and stimulation/measurement, Project No. 1711044801) under the superintendence of National Research Foundation of Korea.

BACKGROUND

1. Field

The present disclosure relates to a system for applying and measuring a quantitative impact, and more particularly, to a quantitative impact control and measurement system for precisely applying a desired impulse.

2. Description of the Related Art

The need for a system that applies precise impacts for the purpose of experimentation, therapy, and the like has been steadily emerging. In particular, precise impact control and measurement systems are being discussed for animal testing to check the changes in the human body caused by external impacts such as traumatic brain injury (TBI).

Traumatic brain injury refers to brain tissue damage caused by external physical impacts or acceleration/deceleration movements of the brain, and it causes loss or alteration of consciousness and resultantly causes impaired cognitive or physical function.

It is estimated that about 1.7 million patients suffers from the traumatic brain injury per year in the United States, and the costs directly and indirectly associated with it are significant, resulting in a major medical/economic/social problem. Even slight brain damage may develop into degenerative brain diseases such as Parkinson's disease and dementia.

A conventional model widely used in animal experiments to study the traumatic brain injury is a weight-drop model. In the weight-drop model, an anesthetized animal is located on a bed made of sponge or the like, and an impact is applied to the head of the animal by freely dropping a weight above the head along a guide tube. In order to control the applied impulse, the weight of the freely-dropped weight or the height of the weight is adjusted. However, in this way, it is difficult to precisely apply a desired impulse, and the actual impulse should be indirectly estimated.

Thus, especially in the field of traumatic brain injury research, it is necessary to provide a precise impact control system for animal experimentation in order to precisely analyze the correlation between the degree of brain damage and external impact and to develop a therapeutic agent according to study of brain tissue damage mechanism.

RELATED LITERATURES

Patent Literature (Patent Literature 1) U.S. Pat. No. 9,808,193

SUMMARY

The present disclosure is designed to solve the above problems of the prior art and the present disclosure is directed to providing a quantitative impact control and measurement system for precisely applying a desired impact.

In an aspect of the present disclosure, there is provided a quantitative impact control and measurement system, comprising: an impactor configured to apply an impact to a target; a control device configured to control movement of the impactor; an acceleration sensor mounted to a base of the impactor; and an impact sensor mounted to a terminal of the impactor, wherein the control device calculates an impact actually applied to the target from signals measured through the acceleration sensor and the impact sensor.

According to an embodiment of the present disclosure, the control device may match a difference in magnitude and phase of a profile of the signal measured through the acceleration sensor and a profile of the signal measured through the impact sensor, and then calculate a force change profile according to time by subtracting the profile of the signal measured through the acceleration sensor from the profile of the signal measured through the impact sensor.

According to an embodiment of the present disclosure, the control device may quantitatively calculate an impulse from the force change profile according to time.

According to an embodiment of the present disclosure, the quantitative impact control and measurement system may further comprise a target adjustment device configured to adjust an impact point of the impactor.

According to an embodiment of the present disclosure, the quantitative impact control and measurement system may further comprise a pair of target lasers configured to indicate the impact point of the impactor, wherein the pair of target lasers may allow laser beams to coincide with each other only at the impact point set by the target adjustment device.

According to an embodiment of the present disclosure, the quantitative impact control and measurement system may further comprise a supporting bed configured to support the target.

According to an embodiment of the present disclosure, the impactor may apply an impact to the target by movement of a piston in a pneumatic cylinder.

According to an embodiment of the present disclosure, the quantitative impact control and measurement system may further comprise a speed adjustment device configured to adjust a speed of the impactor.

According to an embodiment of the present disclosure, the speed adjustment device may control the speed of the impactor by adjusting an opening degree of a speed valve to change an air flow.

According to an embodiment of the present disclosure, the impact sensor may be a power sensor.

According to an embodiment of the present disclosure, the quantitative impact control and measurement system may further comprise an impactor tip disposed at a lower portion of the impact sensor and having a curved shape.

The impact control and measurement system according to various embodiments of the present disclosure may quantify the impact and precisely control the applied impact. In addition, the impact control and measurement system proposed in the present disclosure may measure only the applied impulse free from noise by using an acceleration sensor and an impact sensor. By doing so, the impact control and measurement system of the present disclosure may be used to observe changes in cells and tissues that occur differently depending on the impulse and to study relationships with related diseases and treat the diseases.

The effects obtainable from the present disclosure are not limited to the effects mentioned above, and other effects not mentioned herein will be clearly understood by those skilled in the art from the following disclosure.

DETAILED DESCRIPTION

Figure 1:
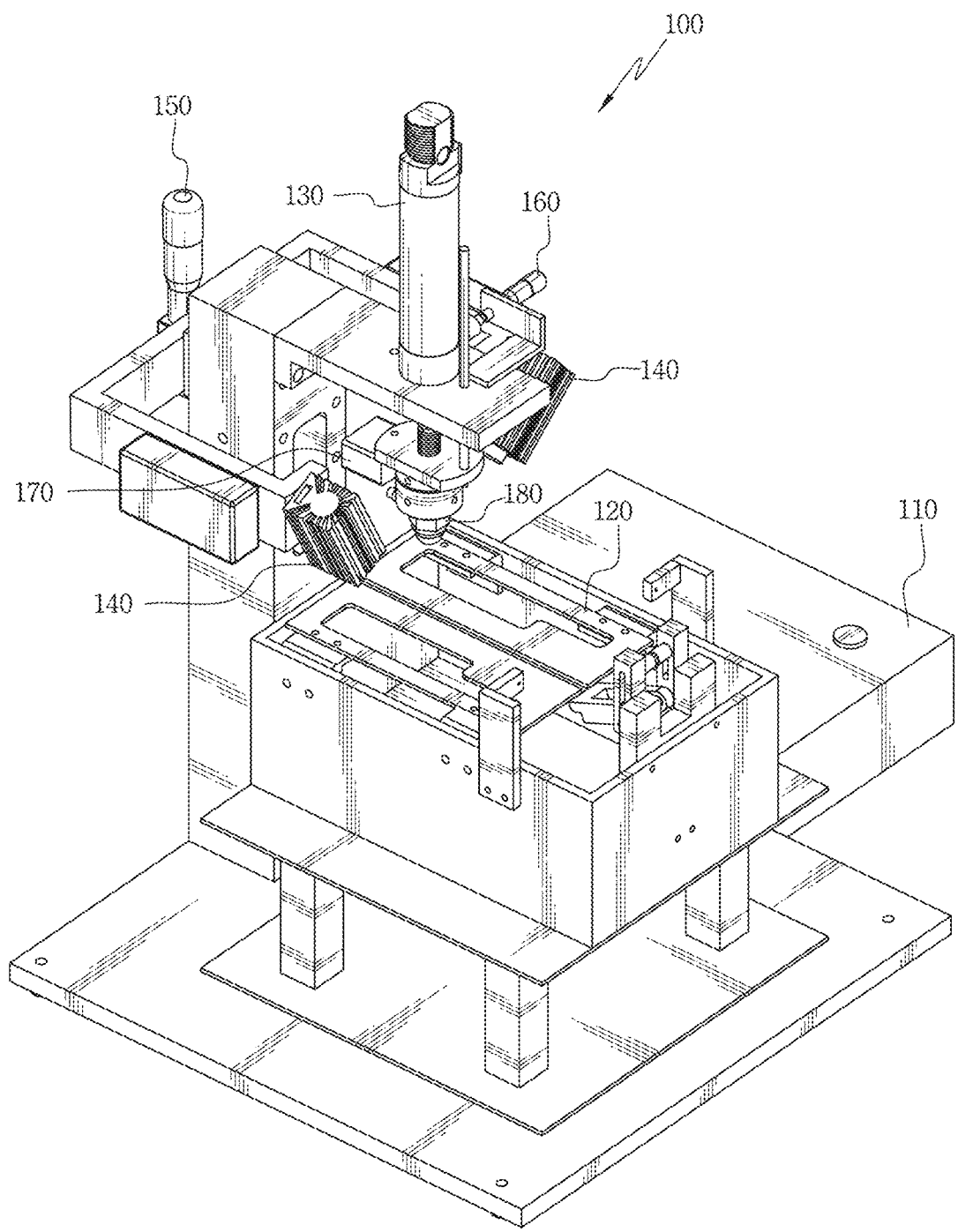
FIG. 1 is shows an impact control system according to an embodiment of the present disclosure.

Advantages and features of the present disclosure and their solutions will be more apparent from the following detailed description and embodiments taken in conjunction with the accompanying drawings. However, the present disclosure is not limited to the embodiments disclosed below but may be implemented in various ways, and the embodiments are just for more perfect disclosure and better understanding to those having ordinary skilled in the art. The present disclosure is defined just by the scope of the appended claims.

The shapes, sizes, ratios, angles, numbers, and the like disclosed in the drawings for describing the embodiments of the present disclosure are just illustrative, and thus the present disclosure is not limited thereto. In addition, in explaining the present disclosure, a detailed description of a related art will be omitted if it is determined that the gist of the present disclosure may be unnecessarily obscured by the description. Where the terms "comprising", "including", "having", and the like are used in this specification, other portions may be added as long as "only" is not used. If any component is expressed in the singular form, this expression includes the case where the component is provided in plural, unless clearly stated otherwise.

In interpreting a component, it is construed to include an error range even if it is not explicitly expressed.

In the description in relation to a positional relationship, for example, if the positional relationship between two portions is described using 'on', 'above', 'under', 'aside', or the like, at least other portion may be located between two portions as long as 'just' or 'directly' is not used.

If an element or layer is referred to as being "on" another element or layer, it includes all cases where still another layer or element is interposed just on another element or layer or between the elements. Like reference numerals denote like elements throughout the specification.

Even though the terms "first", "second", and the like are used for describing various components, the components are not limited to the terms. These terms are just used for distinguishing one component from another. Therefore, a first component mentioned herein may also be used as a second component within the scope of the present disclosure.

The size and thickness depicted in the figures are just for convenience of explanation, and the present disclosure is not necessarily limited to the size and thickness depicted in the figures.

Features of various embodiments of the present disclosure may be coupled to or combined with each other partially or wholly and may be technically linked and operated in various ways as being easily understood by those having ordinary skill in the art. In addition, embodiments may be implemented independently or associated together.

Hereinafter, an impact control system according to a preferred embodiment of the present disclosure and its operation principle will be described with reference to the accompanying drawings. The following description is directed to an impact control system serving as a system for inducing traumatic brain injury in animal experiments, but the present disclosure may be applied to various fields requiring quantitative impact control and measurement, without being limited thereto.

FIG. 1 shows an impact control system 100 according to an embodiment of the present disclosure.

Specifically, referring to FIG. 1, the impact control system 100 according to an embodiment of the present disclosure includes a control device 110, a supporting bed 120, a pneumatic cylinder 130, a target laser 140, a target adjustment device 150, a speed adjustment device 160, an acceleration sensor 170 and an impact sensor 180.

The control device 110 receives and amplifies a signal measured by the acceleration sensor 170 and the impact sensor 180, and transmits the amplified signal to a computing device (for example, a computer) through a DAQ device. In addition, the control device 110 may receive a control signal from the computing device through the DAQ device and control the operation of a piston inside the pneumatic cylinder 130. By controlling the operation of the piston, the movement of an impactor 610 may be controlled resultantly. According to another embodiment, the control device 110 may include the functions of both the DAQ device and the computing device to control the application of an impact as described below and to process a profile measured by the acceleration sensor 170 and the impact sensor 180 to quantitatively calculate an impulse.

Figure 2:
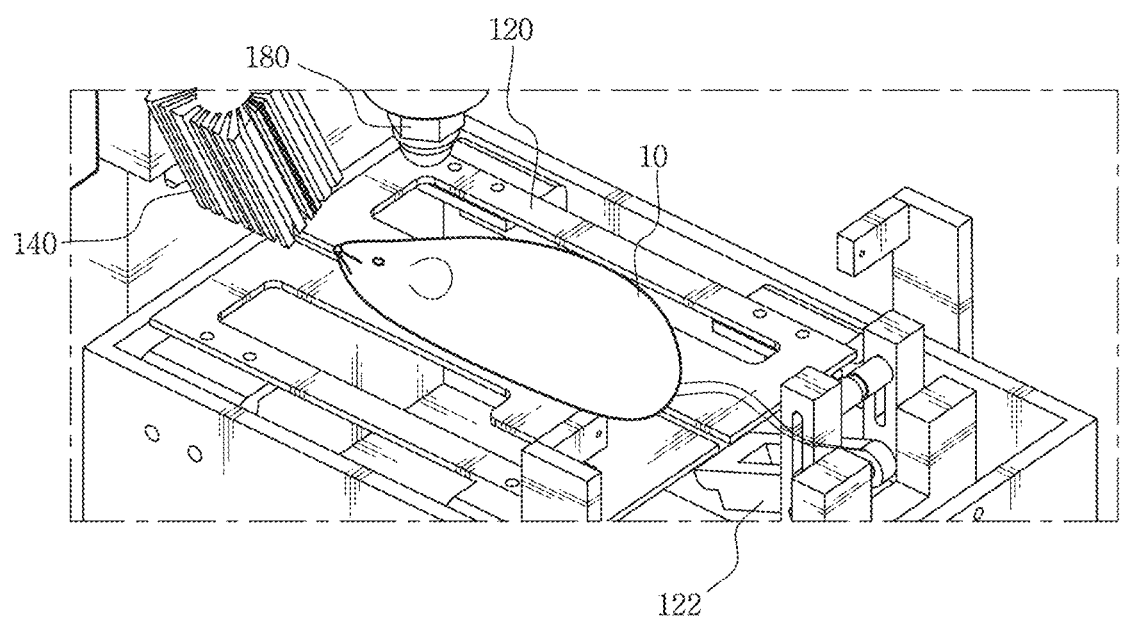
FIG. 2 shows a supporting bed of the impact control system according to an embodiment of the present disclosure.

The supporting bed 120 serves to support a target (for example, an experiment subject 10) to which the impact is to be applied. According to an embodiment of the present disclosure, in order to prevent a rebound effect (a phenomenon that a weight hits the head again due to the elasticity of a string on which the weight is hanging) that is a drawback of a weight-drop model, when the impact is applied, the supporting bed 120 may be split so that the experiment subject 10 falls. As shown in FIG. 2, the supporting bed 120 may have a hinge structure for enduring the load of the experiment subject 10 at both sides as a gravity compensation mechanism using through a spring structure 122.

The pneumatic cylinder 130 includes a piston that is moved by a compressed air. According to an embodiment of the present disclosure, the operation of the piston may be controlled by the control device 110.

Figure 6:
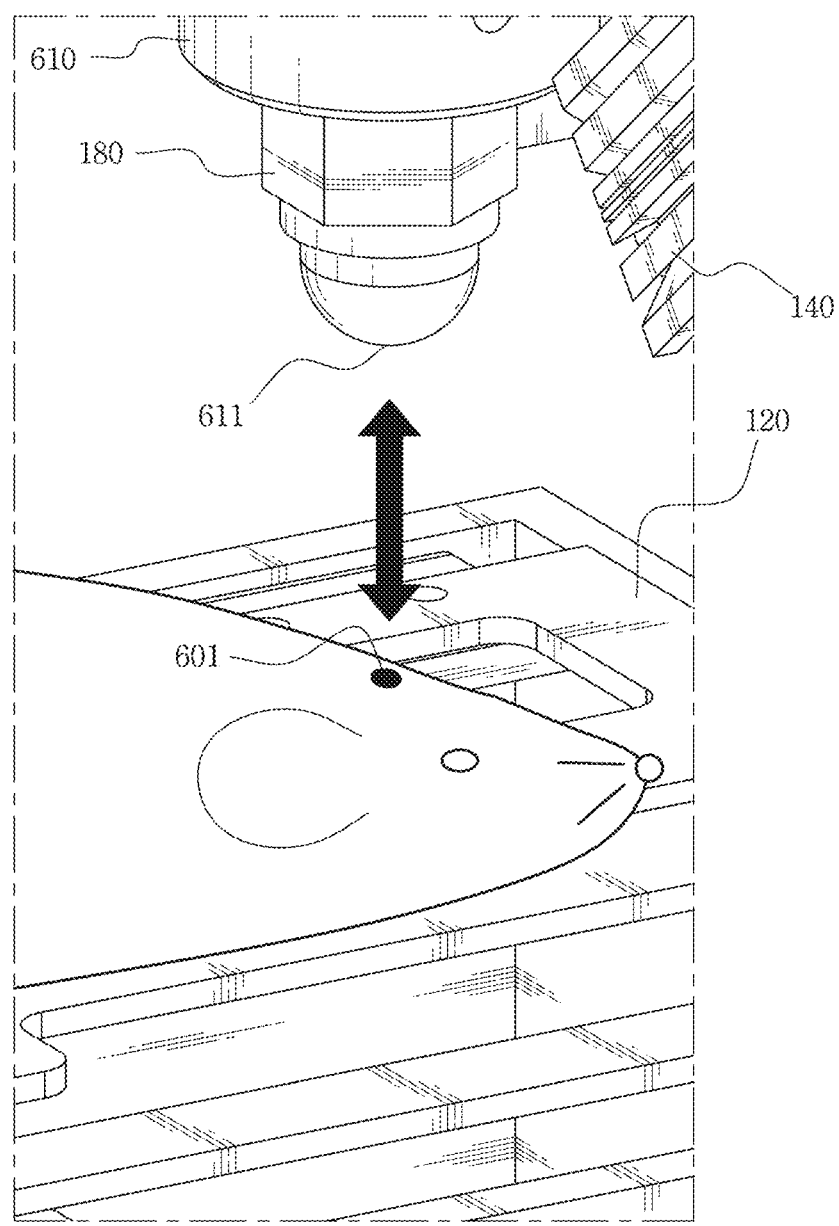
FIG. 6 is an enlarged view showing the impactor of the impact control system according to an embodiment of the present disclosure.

A laser beam formed by the target laser 140 determines a lateral position to which the impact is applied, and simultaneously maintains a preset distance between the impactor 610 and the experiment subject 10. According to an embodiment of the present disclosure, the point at which the impact is applied may be set by the target adjustment device 150, and as shown in FIG. 6, two laser beams of the pair of target lasers 140 located with left and right slopes coincide with each other only at the selected distance.

The target adjustment device 150 may adjust the point where the impact is applied. The target adjustment device 150 may be a micrometer for precisely controlling the point where the impact is applied.

The speed adjustment device 160 adjusts the opening degree of a speed valve by means of a distance in order to adjust an impact applying speed. For example, the speed adjustment device 160 may be a micrometer for precisely adjusting the opening degree of the speed valve by means of a distance. According to an embodiment of the present disclosure, the distance between the impactor 610 and the experiment subject 10 may be fixed by the target adjustment device 150 at the impact control system 100, and only the speed adjustment device 160 may be used for speed control. According to another embodiment, the speed adjustment device 160 may be omitted, and its function may be implemented digitally in a computing device such as a computer to set the speed.

The acceleration sensor 170 is a sensor device for measuring the change (acceleration) of the speed, and may be provided at a base of the impactor 610. According to an embodiment of the present disclosure, an impulse may be quantified by extracting a profile measured by the acceleration sensor 170 and comparing the extracted profile with a profile measured by the impact sensor 180 to extract an actually applied force, as explained later. The acceleration sensor 170 may be connected to the control device 110 to transmit the measured signal.

The impact sensor 180 is a kind of power sensor and may be attached to a terminal of the impactor 610. The impact sensor 180 may be attached to the terminal of the impactor 610 to measure the force when the experiment subject 10 is hit. As shown in FIG. 6, an impactor tip 611 may be further included under the impact sensor 180. The impactor tip 611 may be formed to have a curved shape, for example a hemispherical shape, so as not to damage the outer side of the experiment subject 10 and to prevent the impact from being distributed. The impact sensor 180 may be connected to the control device 110 to transmit the measured signal.

In a conventional weight-drop model widely used in the art for traumatic brain injury studies, an anesthetized animal is located on a bed such as a sponge, and an impact is applied to the head by dropping a weight located above the animal along a guide tube. In order to control the impulse applied in the weight-drop model, it is needed to adjust the weight of the freely-dropped weight or the dropping height of the weight.

However, the actual impact applied to the target animal is determined by transferring a part of the momentum of the freely-dropped weight (momentum transfer). Even if the load of the freely-dropped weight or the height of the dropping height of the weight is adjusted, it is hard to regard that the momentum of the freely-dropped weight is entirely transferred to the target animal.

In order to measure the impulse transferred to the actual target animal, in the prior art, an impact sensor is attached onto the head of the target animal, or the applied impact is indirectly measured by means of image analysis.

In the method of attaching an impact sensor onto the head of the target animal, it is difficult to attach the impact sensor, and it is also difficult that the impact sensor keeps perpendicular to the impactor while the impact is being applied, even though the impact sensor is attached like a helmet. In addition, if the impact sensor is attached to the head of the target animal, since the impact sensor is located between the dropped weight and the target animal, the impact sensor absorbs a part of the impact, and thus it is hard to regard that the impact received by the impact sensor is entirely transferred to the target animal.

In the method of indirectly measuring the applied impact by means of image analysis, a marker for capturing image such as a checker board is attached to the target animal to analyze the head movement of the target animal with a high-speed camera, and sensor information is added to indirectly measure the applied impulse. However, in this method, it is just possible to indirectly deduce the impulse, and it is difficult to quantify the impulse.

The present disclosure proposes a method of quantifying the impulse by obtaining a noise-free force change profile according to time by using the impact sensor 180 attached to the terminal of the impactor 610 and the acceleration sensor 170 provided at the base of the impactor 610. Hereinafter, the process of obtaining a noise-free force change profile according to time will be described with reference to FIGS. 3A to 3E.

FIGS. 3A to 3E show profiles measured by the impact control system 100 according an embodiment of to the present disclosure. For example, the profiles of FIGS. 3A to 3D may be obtained using the acceleration sensor 170 and the impact sensor 180 of the impact control system 100.

Figure 3A:
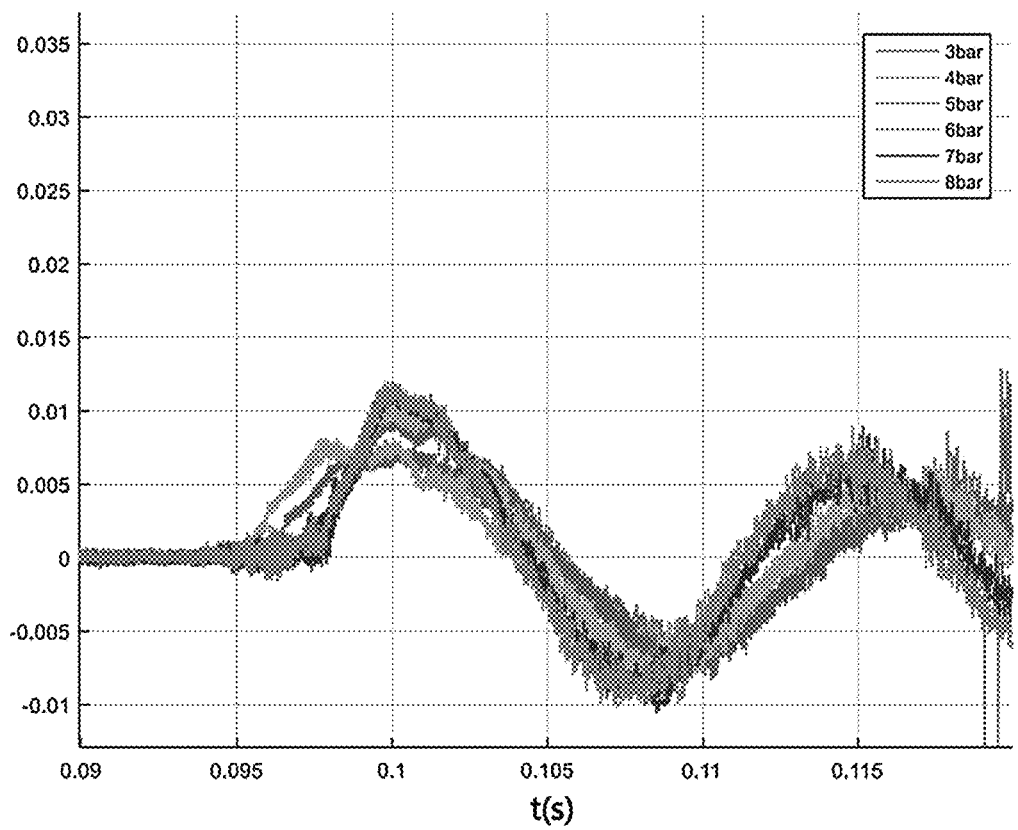
FIGS. 3A to 3E show profiles measured by the impact control system according to an embodiment of the present disclosure.

Referring to FIG. 3A, a force change graph according to time, obtained by the impact sensor 180 attached to the impactor 610, is shown. The graph of FIG. 3A shows a profile obtained by acceleration of the impact sensor 180 without an actual impact. One of good ways to quantify the impulse actually applied to the experiment subject 10 is to attach the impact sensor 180 to the terminal of the impactor 610 so that the impact sensor 180 measures the force generated when an impact is applied to the experiment subject 10 according to time. However, as shown in FIG. 3A, if the impact sensor 180 is attached to the terminal of the impactor 610 that is moving, noise is generated since force is measured even though an impact is not applied, and thus it is difficult to accurately measure the impact. For example, considerable acceleration (for example, 300 g to 400 g) is required to reach a desired speed (for example, ~2.5 m/s) at a distance of less than 10 mm, and this acceleration is exhibited as noise at the impact sensor 180 that measures a force. In addition, as shown in FIG. 3A, though the pressure of the pneumatic cylinder is changed, the noise measured by the impact sensor 180 has a similar pattern.

Thus, in order to measure only the impact applied to experiment subject 10, a method of compensating for the noise is required. To this end, the present disclosure suggests a method of providing the acceleration sensor 170 to the impactor 610.

Figure 3B:
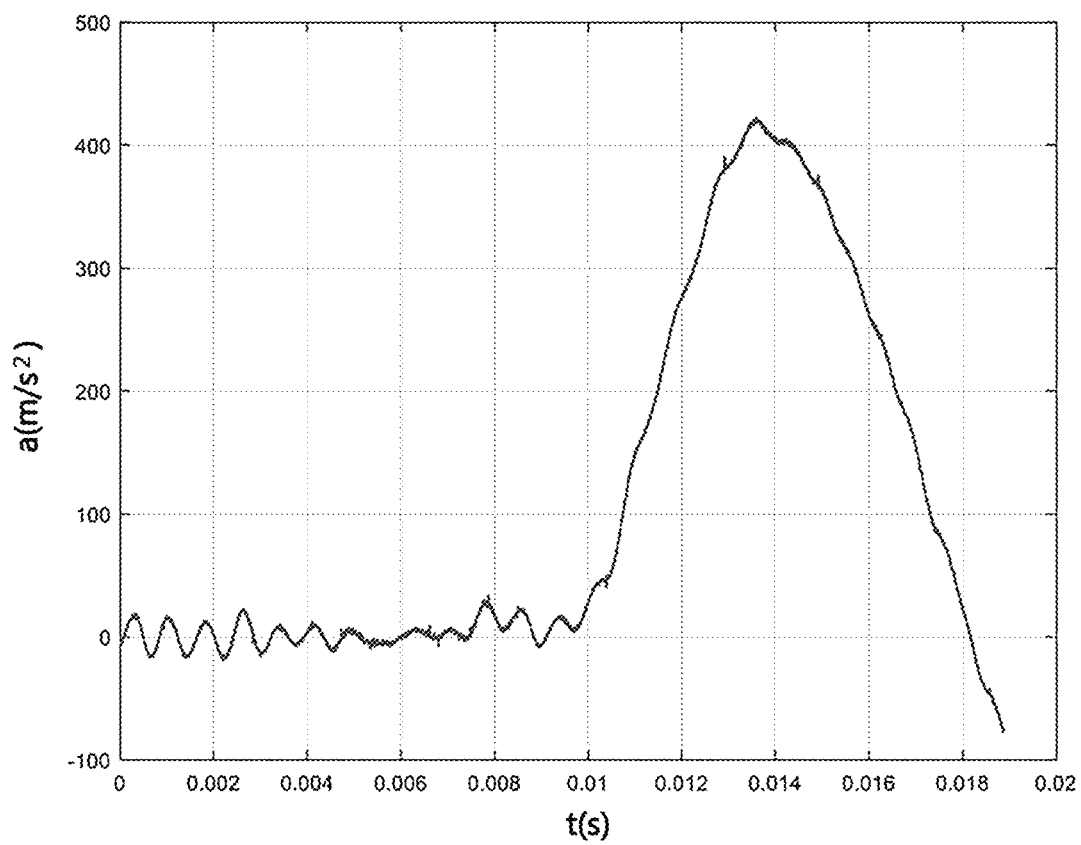

Referring to FIG. 3B, an acceleration change graph according to time, obtained by the acceleration sensor 170 attached to the base of the impactor 610, is depicted. The graph of FIG. 3B shows a profile obtained by the acceleration sensor 170 in the absence of an actual impact.

Figure 3C:
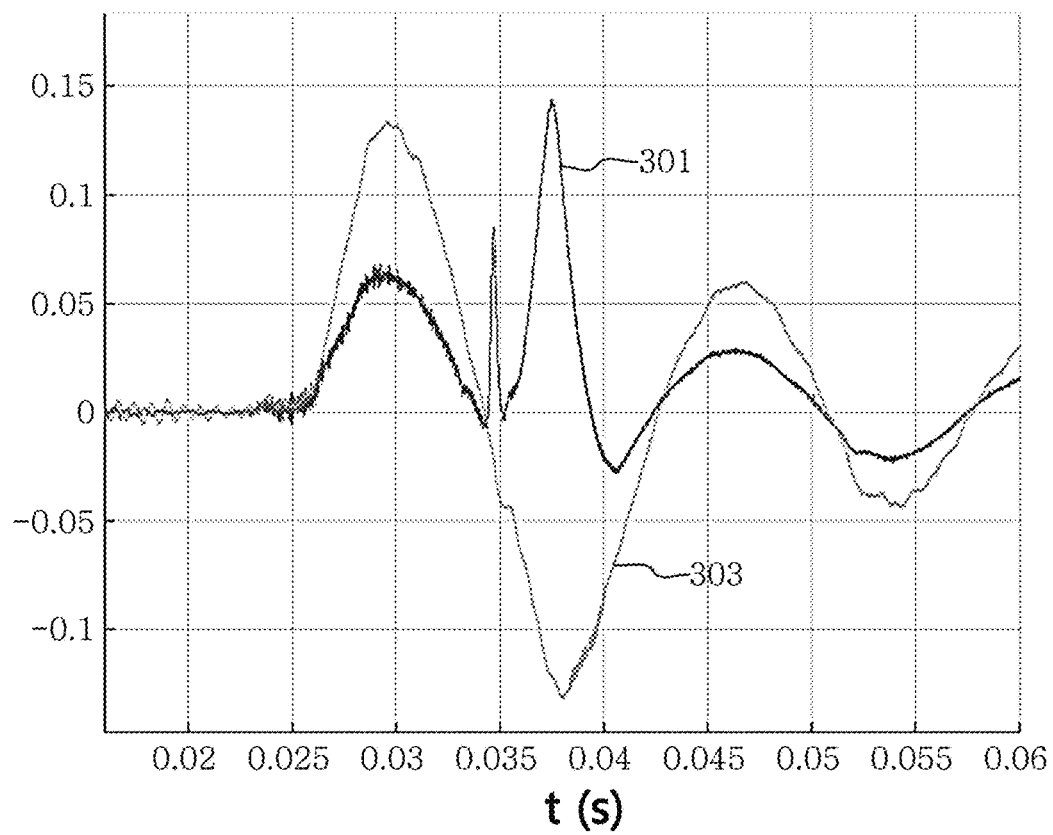

Referring to FIG. 3C, a profile 301 actually measured at the impact sensor 180 and a profile 303 measured by the acceleration sensor 170 while the impactor 610 applies an impact to the experiment subject 10 are shown. In order to measure only the actually applied impact by the impact sensor 180, the noise must be compensated. For this, the actually applied force may be obtained by extracting the profile measured by the acceleration sensor 170 and then comparing the measured profile with the profile of the impact sensor 180. The acceleration sensor 170 may extract a base line and integrate the acceleration to directly calculate and measure the speed of the impactor 610 when the impact is applied. However, as shown in FIG. 3C, since two sensors have different modalities, the measured profiles may have different magnitudes and phases.

Figure 3D:
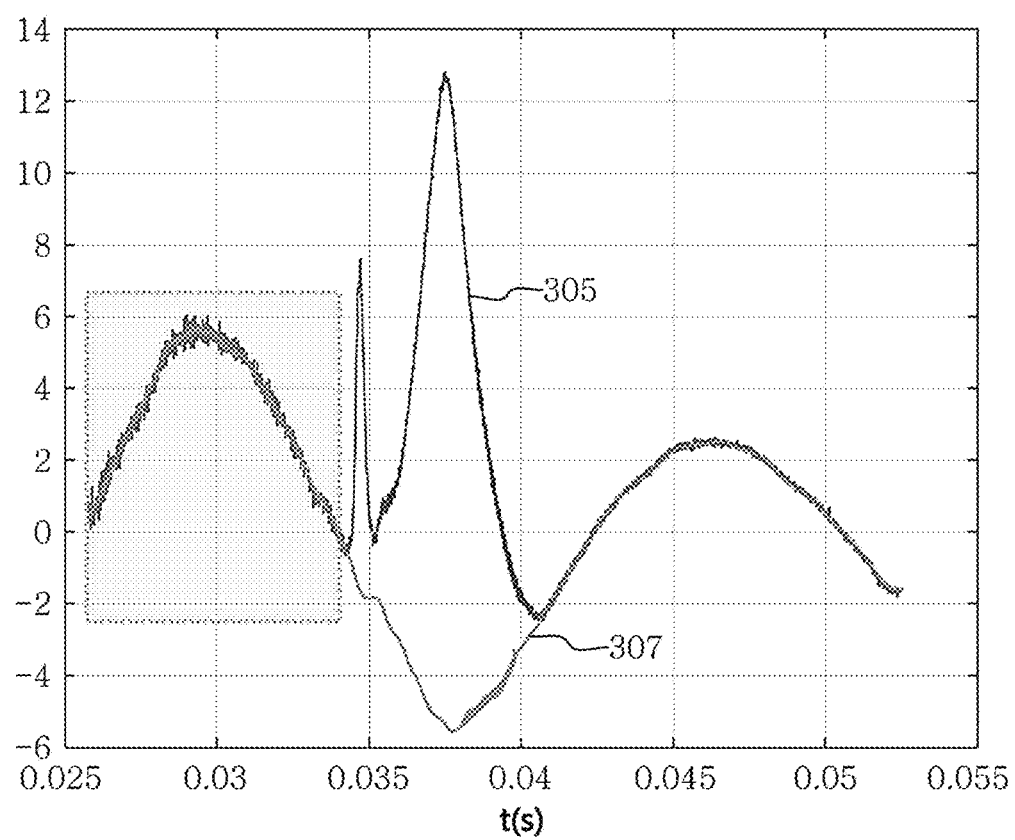

Referring to FIG. 3D, a profile 305 of the impact sensor 180 and a profile 307 of the acceleration sensor 170 after the different magnitudes and phases of the profile are matched are shown. Since the impact sensor 180 and the acceleration sensor 170 have different modalities as described above, only a profile for a noise region is locally extracted for profile matching, and the difference in effective mass and phase may be calculated by applying a nonlinear optimization method thereto. In other words, the point at which the impact occurs may be found for matching the profiles of the two sensors, and a value with which the product of the acceleration profile and the effective mass is most approximate to the profile of the impact sensor based on the profile up to this point may be found using an optimization method. As shown in FIG. 3D, since the value of the impact sensor 180 changes abruptly near 0.034 (s), it may be found that this is the point at which the impact is applied. The difference in magnitude and phase may be matched by applying the optimization method so that the profile 305 of the impact sensor 180 and the profile 307 of the acceleration sensor 170 before the impact occurrence point of 0.034 (s) are approximated.

Figure 3E:
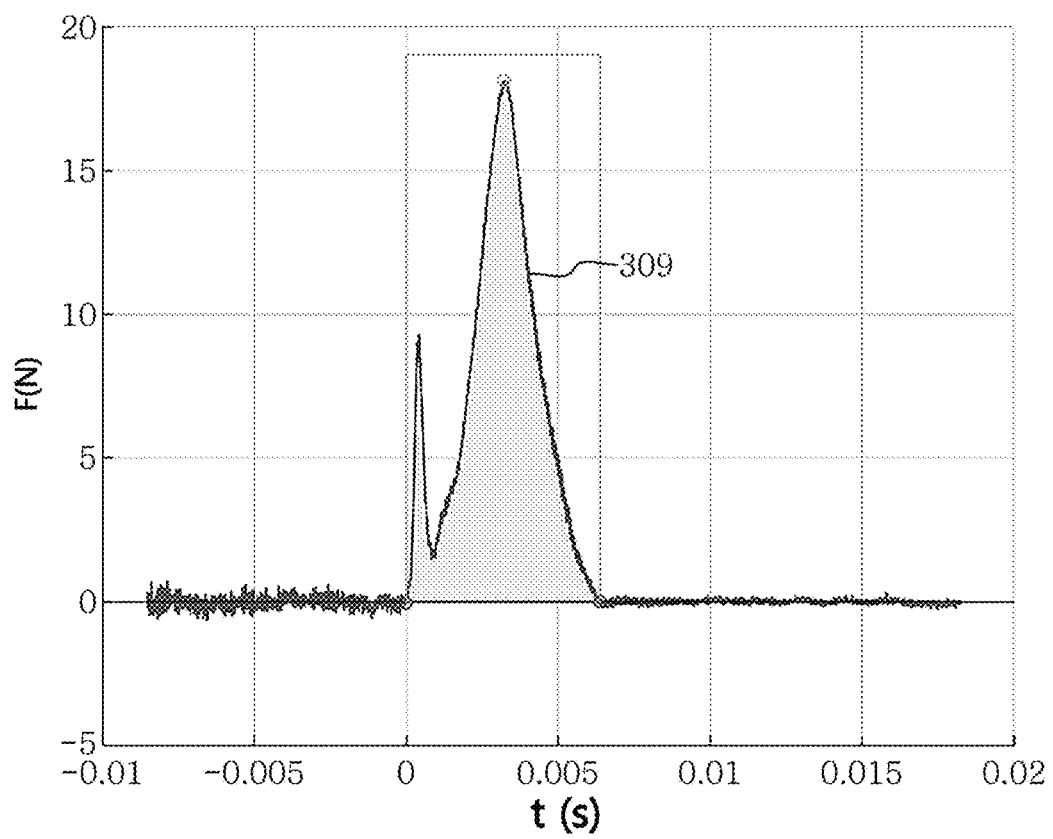

Referring to FIG. 3E, a profile 309 of an actually applied force free from noise is shown. As shown in FIG. 3D, if the profile of the acceleration sensor 170 is subtracted from the profile of the impact sensor 180 after the difference in magnitude and phase is matched, the profile of the force 309 actually applied to the impact sensor 180 by using the profile of the acceleration sensor 170 as a base line may be calculated. As shown in FIG. 3E, a flat base line may be obtained, and the impulse may be quantitatively calculated from the profile 309 of the actually applied force free from noise.

Meanwhile, referring to FIGS. 3C to 3E, if an impact is applied to a brain having a hinge structure by a vertebra like a mouse, the profile of the applied force may appear multiple times (for example, twice).

As described above with reference to FIGS. 3A to 3E, the impulse may be quantified from the profile of the force actually applied to experiment subject 10. In order to observe changes of cells and tissues according to the quantified impulse and to check the correlation with related phenomena (a disease expression marker and the like) through the observation, it is also important to precisely control the impulse to be accurately applied to the experiment subject 10.

A controlled cortical impact (CCI) product is being used as a system to control the impact applied. The CCI product may adjust the speed and depth of the impactor, but it is not easily used in a closed and diffuse head injury model.

Figure 4:
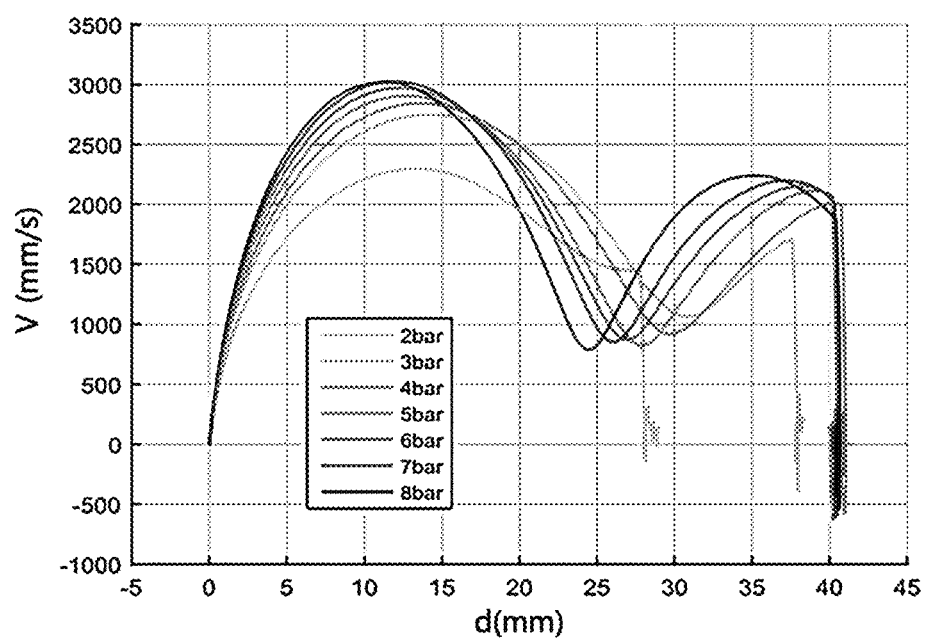
FIG. 4 shows a relationship between a distance and a speed according to an inner pressure of a pneumatic cylinder of the impact control system according to an embodiment of the present disclosure.

FIG. 4 shows the relationship between the distance and the speed according to an internal pressure of the pneumatic cylinder 130 of the impact control system 100 according to an embodiment of the present disclosure. For example, FIG. 4 shows the relationship between the distance and the speed, obtained through experiments with different pressures in a case where the stroke of the pneumatic cylinder 130 is 40 mm.

In the conventional free-drop method, the applied impact is controlled by the extrusion of the pneumatic cylinder 130. However, the amount of impact is more heavily influenced by the applied distance and speed than the pressure of the pneumatic cylinder 130. As shown in FIG. 4, it may be found that the speed difference of the impactor is not greater than the change of the pressure ratio at a distance of 10 mm and at a pressure of 3 bar or more. Since the pressure of the pneumatic cylinder 130 is related to the static loading, the speed of the piston is important for the momentum. In addition, referring to FIG. 4, it may be found that the speed of the piston is also related to the distance between the pneumatic cylinder 130 and the object to which the impact is applied.

In the end, the amount of impact is related to the speed of the impactor 610, and thus it is important to adjust the point where the impact is applied and the speed of the impactor 610 in order to adjust the applied impact.

Figure 5:
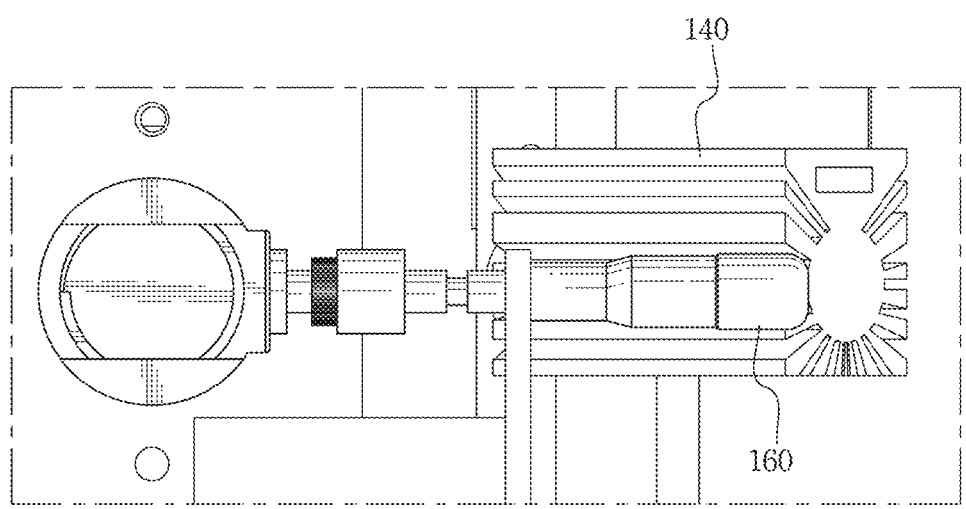
FIG. 5 shows a speed adjustment device for adjusting a hitting speed of an impactor of the impact control system according to an embodiment of the present disclosure.

FIG. 5 shows the speed adjustment device 160 for adjusting a hitting speed of the impactor 610 of the impact control system 100 according to an embodiment of the present disclosure.

Referring to FIG. 5, the speed adjustment device 160 adjusts the opening degree of the speed valve to change a flow rate when air is discharged, thereby controlling the speed. The speed adjustment device 160 may be a micrometer that precisely adjusts the opening degree of the speed valve by means of a distance. According to an embodiment of the present disclosure, Table 1 shows an example where the speed and impact of the impactor 610 applied to the experiment subject 10 (for example, the head of a mouse) according to the opening degree of the speed valve of the speed adjustment device 160 when the distance of the point where the impact is applied is fixed to 10 mm at the target adjustment device 150 depicted in FIG. 7.

TABLE 1

| Valve Opening (mm) | V (m/s) | Impact (mNs) | Primary (mNs) | Secondary (mNs) | Peak F (N) | Duration (ms) |
|---|---|---|---|---|---|---|
| 0.5 | 0.87 | 10.27 | 0.56 | 9.71 | 1.42 | 0.76 |
| 1 | 1.43 | 14.76 | 1.46 | 13.30 | 4.06 | 0.83 |
| 1.5 | 1.73 | 17.16 | 1.88 | 15.29 | 5.26 | 0.93 |
| 2 | 1.87 | 20.09 | 3.19 | 16.89 | 6.16 | 2.33 |
| 2.5 | 2.10 | 26.29 | 6.49 | 19.80 | 7.12 | 3.47 |
| 3 | 2.17 | 26.25 | 2.50 | 23.75 | 7.70 | 0.98 |
| 3.5 | 2.27 | 24.36 | 4.49 | 20.00 | 8.12 | 1.24 |
| 4 | 2.35 | 27.79 | 2.80 | 24.99 | 10.02 | 0.73 |
| 4.3 | 2.66 | 42.90 | 42.96 | −0.06 | 17.70 | 6.37 |
| 4.5 | 2.68 | 46.62 | 46.55 | 0.07 | 19.30 | 5.95 |

Referring to Table 1, the speed is changed according to the opening degree of the speed valve of the speed adjustment device 160, and thus the degree of impact is changed. In particular, if an impact is applied to a brain of a mouse having a hinge structure connected to the vertebrae, first and second impacts may be detected as shown in Table 1. According to another embodiment, the opening degree of the speed valve may be controlled digitally from the computing device. As a result, the speed of the impact 610 is controlled by adjusting the opening degree of the speed valve, thereby controlling the impulse applied to the experiment subject 10.

Figure 7:
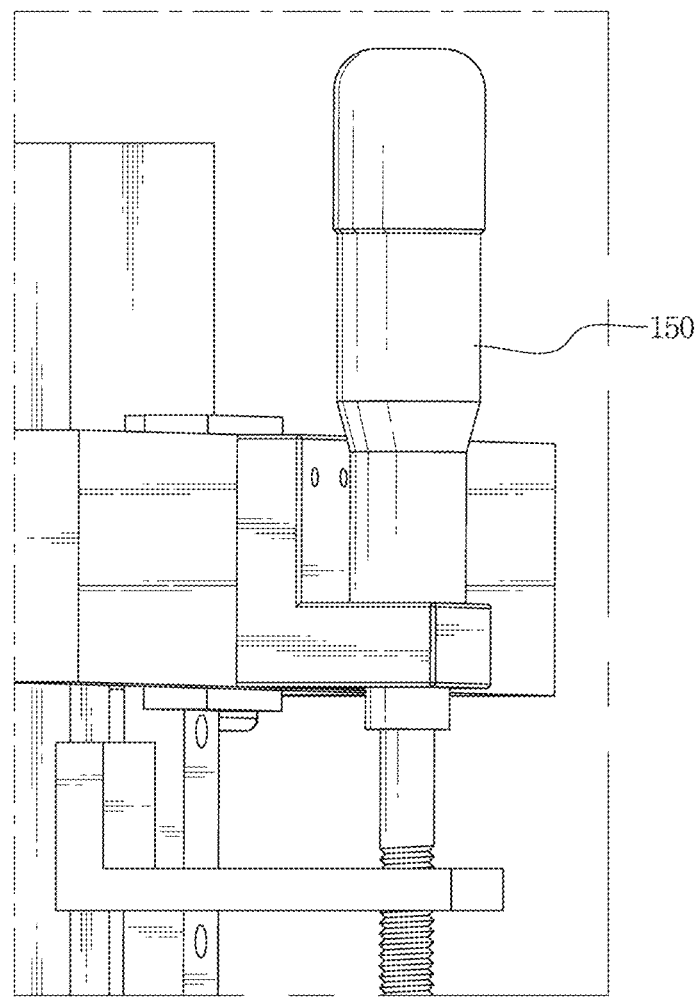
FIG. 7 shows a target adjustment device for adjusting a hitting position of the impactor of the impact control system according to an embodiment of the present disclosure.

FIG. 6 is an enlarged view showing the impactor 610 of the impact control system 100 according to an embodiment of the present disclosure. FIG. 7 shows the target adjustment device 150 for adjusting a hitting position of the impactor 610 of the impact control system 100 according to an embodiment of the present disclosure.

Referring to FIGS. 6 and 7, the point at which the impact is applied in the experiment subject 10 may be adjusted using the target adjustment device 150. The laser beams 601 of the left and right target lasers 140 may coincide with each other only at the distance set by the target adjustment device 150, and the application of the impact may be controlled by positioning the experiment subject 10 by using the coincided laser beams 601 as an impact applying point. According to an embodiment of the present disclosure, the distance (a red arrow) between the laser beams 601 coinciding at the impactor tip 611 by the target adjustment device 150 may be adjusted to 10 mm, and the impulse may be adjusted by controlling the speed by the speed adjustment device 160 in a state where the target distance is fixed to 10 mm.

In the specific embodiments described above, components included in the present disclosure have been expressed in the singular or plural form in accordance with the proposed specific embodiments. However, the singular or plural form is selected appropriately for the sake of convenience of description, and it should be understood that the embodiments described above are not limited to the singular or plural form. Even though any component is expressed in the plural form, the component may be provided singular. Also, even though any component is expressed in the singular form, the component may be provided in plural.

Meanwhile, even though the specific embodiments have been described above, various changes and modifications may be made thereto without departing from the technical scope of the present disclosure involved in the embodiments. Thus, the scope of the present disclosure should not be construed as limited to the embodiments described above, but should be determined by the scope of the appended claims and their equivalents.

[Reference Signs]

| | |
|---|---|
| 10: experiment subject | 100: impact control system |
| 110: control device | 120: supporting bed |
| 130: pneumatic cylinder | 140: target laser |
| 150: target adjustment device | 160: speed adjustment device |
| 170: acceleration sensor | 180: impact sensor |
| 610: impactor | 611: impactor tip |

What is claimed is:

1. A quantitative impact control and measurement system, comprising:
    an impactor configured to apply an impact to a target;
    a control device configured to control movement of the impactor;
    an acceleration sensor mounted to a base of the impactor; and
    an impact sensor mounted to a terminal of the impactor,
    wherein the control device calculates an impact actually applied to the target from signals measured through the acceleration sensor and the impact sensor; and
    wherein the control device matches a difference in magnitude and phase of a profile of a signal measured through the acceleration sensor and a profile of a signal measured through the impact sensor, and then calculates a force change profile according to time by subtracting the profile of the signal measured through the acceleration sensor from the profile of the signal measured through the impact sensor.

2. The quantitative impact control and measurement system according to claim 1,
    wherein the control device quantitatively calculates an impulse from the force change profile according to time.

3. The quantitative impact control and measurement system according to claim 1, further comprising:
    a target adjustment device configured to adjust an impact point of the impactor.

4. The quantitative impact control and measurement system according to claim 3, further comprising:
    a pair of target lasers configured to indicate the impact point of the impactor,
    wherein the pair of target lasers allow laser beams to coincide with each other only at the impact point set by the target adjustment device.

5. The quantitative impact control and measurement system according to claim 1, further comprising:
    a supporting bed configured to support the target.

6. The quantitative impact control and measurement system according to claim 1,
    wherein the impactor applies an impact to the target by movement of a piston in a pneumatic cylinder.

7. The quantitative impact control and measurement system according to claim 6, further comprising:
    a speed adjustment device configured to adjust a speed of the impactor.

8. The quantitative impact control and measurement system according to claim 7,
    wherein the speed adjustment device controls the speed of the impactor by adjusting an opening degree of a speed valve to change an air flow.

9. The quantitative impact control and measurement system according to claim 1,
    wherein the impact sensor is a power sensor.

10. The quantitative impact control and measurement system according to claim 1, further comprising:
    an impactor tip disposed at a lower portion of the impact sensor and having a curved shape.

* * * * *